United States Patent [19]

Cerny

[11] Patent Number: 4,900,780

[45] Date of Patent: Feb. 13, 1990

[54] ACELLULAR RESUSCITATIVE FLUID

[75] Inventor: Lawrence C. Cerny, Utica, N.Y.

[73] Assignee: Masonic Medical Research Laboratory, Utica, N.Y.

[21] Appl. No.: 198,291

[22] Filed: May 25, 1988

[51] Int. Cl.$^4$ .................... C08L 89/00; C08F 16/00; C07G 7/00

[52] U.S. Cl. ................ 525/54.1; 525/54.24; 530/385; 514/6

[58] Field of Search .................. 525/54.1, 54.24; 530/385; 514/6

[56] References Cited

U.S. PATENT DOCUMENTS

| | | | |
|---|---|---|---|
| 4,336,248 | 6/1982 | Bonhard et al. | 514/6 |
| 4,650,786 | 3/1987 | Wong | 514/6 |
| 4,698,387 | 10/1987 | Schmidt et al. | 525/54.1 |

OTHER PUBLICATIONS

Cerny et al., "A Hydroxyethyl Starch–Hemoglobin Polymer as a Blood Substitute", Clinical Hemorheology, vol. 2, pp. 355–365, 1982.
Cerny et al., "Mixtures of Whole Blood and Hydroxyethyl Starch–Hemoglobin Polymers", Critical Care Medicine, vol. 11, No. 9, pp. 739–743, 1983.
Cerny et al., "A Blood Substitute from Hydroxyethyl Starch and Hemoglobin", Applied Biochemistry and Biotechnology, vol. 10, pp. 151–153, 1984.

*Primary Examiner*—John Kight
*Assistant Examiner*—Nathan M. Nutter
*Attorney, Agent, or Firm*—Darby & Darby

[57] ABSTRACT

An acelluar resuscitative fluid, useful as an artificial blood or blood substitute, is prepared from a modified, high molecular weight starch or a tetronic polyol prepared by the interaction of ethylenediamine and ethylene or propylene oxides, which are converted to their aldehyde form. This material is reacted with a stabilized, stroma free hemoglobin, which has been converted to an oxy-acid or diketone. The resulting solution, after purification, can be administered to an animal in the same manner as whole blood. If desired, the solution of the reaction product with the stabilized hemoglobin can be freeze-dried and later reconstituted by the addition of water to provide the administrable fluid.

20 Claims, 2 Drawing Sheets

ACELLULAR RESUSCITATIVE FLUID

BACKGROUND OF THE INVENTION

The need for, and desirability of, a blood substitute has become increasingly clear over the last several years. Not only is there a shortage of whole blood available for transfusions, for a variety of reasons, but there is the fear, both real and imagined, of the transmission of communicable diseases through the use of whole blood transfusions. Such diseases include, for example, hepatitis and AIDS.

Still further, there are emergency situations in which whole blood, even if otherwise available, is not present for use. For example, ambulances generally do not have the necessary storage facilities for whole blood. Persons in remote locations, who may require transfusions, including those in space flight, do not have access to banks of whole blood.

In a typical year, ten million units of whole blood are collected for use in transfusions. Of these, approximately 53% are transfused as whole blood. The red blood cells are removed from approximately 15% more of the blood obtained, and these are transfused in the form of the cells. However, whole blood has a finite storage life, even when adequately stored, and approximately 25% of the whole blood collected in any year must be discarded.

While the hemoglobin from this blood to be discarded could be saved, early attempts at using it failed, when fragments of red blood cells, referred to as stroma, were found to clog small blood vessels and cause blockages. Recently, however, filtration processes have been developed to produce a stroma-free hemoglobin.

Since no oxygen transport and transmission system equivalent to hemoglobin has ever been discovered, scientists have long sought means of employing the hemoglobin which is otherwise discarded, even the stroma-free hemoglobin. Efforts in the past have, however, proven unsuccessful.

BRIEF DESCRIPTION OF THE INVENTION

In accordance with the present invention, it has unexpectedly been discovered that by reacting a stabilized form of the stroma-free hemoglobin with high polymer substances, a material is produced which can be employed as an artificial blood or blood substitute. Further, because of the forms in which the material can be produced, it can easily be made available in remote locations. Of great importance is the fact that, since the plasma of the whole blood is not employed, typing of the blood, which often results in extreme delays and even inability to carry out a transfusion, is not required.

In accordance with the present invention, the stroma-free hemoglobin, which is prepared by known techniques, is converted to an oxyacid or a diketone. This form of the hemoglobin is then reacted with a high polymer material.

Two types of high polymer material have been found useful in accordance with the present invention, each having been converted to an aldehyde configuration; the high polymers may be mono-, di-, tri-, or tetra-aldehydes. These high polymers provide the necessary oncotic and rheological properties for the blood substitute.

The first form of high polymer is a starch having a molecular weight in the range of from 60,000 to 450,000 daltons. The starch is substituted to a degree of from 0.2 to 0.9 by hydroxyethylation.

The second type of polymer which can be reacted with the modified hemoglobin is referred to as a tetronic polymer, since it is four-pronged, having four chains radiating from a central moiety. In particular, these tetronic polymers can be formed by reaction of ethylene and propylene oxides with a tetra reactive moiety to provide a polymer polyol with a molecular weight of between 1,650 and 27,000 daltons. This tetronic polyol is also converted to an aldehyde prior to reaction with the modified hemoglobin.

After the reaction of the two components, and the necessary purification, as by dialysis, the solution can be used, as such, for administration to a mammal requiring a transfusion. On the other hand, and frequently more desirably, the solution can be freeze-dried to leave a powder of the reacted hemoglobin-polymer, because it is in an acellular form. This powder is believed to have a substantial storage life, for example, up to five years. Obviously, storage of the powder requires far less space and there is no necessity for exacting storage conditions. When a transfusion is required, the powder can be dissolved in water, at room temperature, and applied almost immediately. Preferably, the water employed to reconstitute the powder, in order to reduce the risk of infection, is distilled, demineralized, or deionized.

DESCRIPTION OF THE PREFERRED EMBODIMENTS

Figure 1:
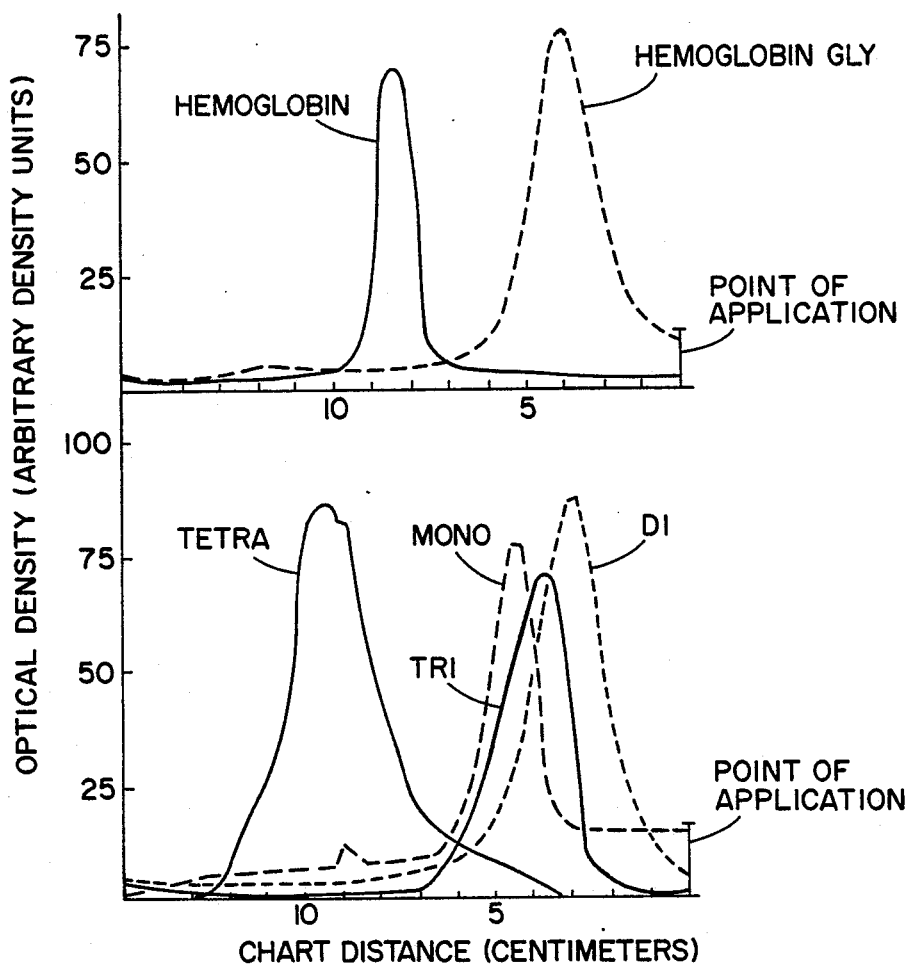
FIG. 1 illustrates the optical density of the acellular resuscitative fluid of the present invention versus chart distance.

In accordance with the present invention, a stroma-free hemoglobin (Hgb), which has been converted to an oxyacid or diketone form, is reacted with one of two high polymers which are in the form of a mono or polyaldehyde, the polyaldehyde being either in the di-, tri-, or tetra- form. The amount of modified hemoglobin and aldehyde containing polymer employed in the reaction is a stoichiometric amount of each, ±10%.

In forming the modified Hgb, the arginine residues of the Hgb are modified with a cyclic dione in a borate buffer in an aqueous solution. The concentration of the solution should be between 1 and 15 grams of Hgb per 100 ml. of solution, the amount of cyclic dione being from 0.02 to 0.3 gm. Sufficient buffer is added to obtain a pH of between 8.0 and 10.0.

Among the cyclic diones which can be employed are 1, 2-cyclohexanedione, 1,3-cyclohexanedione and 1,4-cyclohexanedione. An appropriate buffer for the reaction is sodium borate, but other materials which will provide a buffer, such as phosphates can also be employed. The amount of cyclic dione added is between 0.02 and 0.03 part, by weight, for each 100 ml. of solution.

While maintaining the pH of the solution at between 8 and 10, the reaction mixture is kept above room temperature, for example at a temperature of from 30° to 37° C., for approximately 1 to 4 hours, under an inert atmosphere. Nitrogen is an appropriate atmosphere. The resulting material is dialyzed cold against clean water, usually employing dialysis tubing. The water employed in the dialysis step should be distilled, deionized, or demineralized. The resulting modified Hgb is called Hgb - cyclo.

A second method of stabilizing the Hgb involves its carboxymethylation by alkylation with an oxyacid in the presence of a borohydride. Again, a 1 to 15% aqueous solution of the arginine residue of Hgb is employed and to it are added from 0.1 to 0.5 grams of an oxyacid, which is in a 0.1 to 1.5% aqueous solution which has been neutralized to a pH of 7 with a water soluble hydroxide, such as sodium hydroxide. Among the oxyacids which can be employed in this reaction are glyoxalic acid, pyruvic acid, and oxybutanoic acids.

From 0.1 to 1.5 grams of borohydride is added for each 0.1 to 0.5 grams of the oxyacid solution. The pH of the Hgb solution is adjusted to 7 with a buffer, such as a phosphate buffer. Among the borohydrides which can be employed are cyanoborohydride and sodium borohydride.

The Hgb solution and the solution of oxyacid and borohydride are combined in a ratio of 0.5 to 1.5 moles and are maintained at a pH of 7 for from 1 to 4 hours at room temperature. The solution is then dialyzed against water, employing dialysis tubing, at a temperature of from 30° to 37° C. The water employed in the dialysis should be distilled, deionized, or demineralized. The resulting product is termed Hgb - Gly.

The first type of high polymer with which the modified Hgb can be reacted is a tetronic polymer, which is so called because of its "four-pronged" nature. One type of commercially available material is Tetronic 1307, obtained from BSAF Wyandotte Corp., Wyandotte, Michigan. This is a tetra-alcohol polymer formed by sequential additions of ethylene and propylene oxides to ethylenediamine. The material has a molecular weight in the range of from 1650 to 27000 daltons. Other suitable materials include "Pluronic" polyols from the same company. This polymer is dissolved in dimethyl sulfoxide in a concentration of from 1 to 15% at room temperature. Solvents which can be employed in place of the dimethyl sulfoxide include diethyl and dipropyl sulfoxide.

A carbodiimide is added to the tetronic polymer in an amount of from 0.5 to 1.5 parts for each 10 parts of the starting polymer. Among the carbodiimides which can be employed in this reaction are dicyclohexyl carbodiimide or diphenyl carbodiimide. A trace of a tribasic acid is also added to this solution to render it slightly acidic, a pH of approximately 7. The resulting mixture is stirred at room temperature for at least 12 hours and is then dialyzed in dialysis tubing against water which is either distilled, deionized, or demineralized, in order to insure the elimination of unreacted materials. Generally, this dialysis, which includes several changes of water, requires approximately 24 hours. Any precipitate forming during the dialysis may be removed by filtration.

It has been found that the degree of aldehyde substitution realized is approximately proportional to the time employed in the initial stirring reaction. For example, it has been determined by quantitative analysis, that with approximately 6 hours of stirring, a dialdehyde is formed, while the tetra-aldehyde is formed after approximately 12 hours. The presence of the aldehyde is confirmed by infrared analysis. It has been found that the tetra-aldehyde has the greatest combining capacity for the stabilized Hgb.

The second type of high polymer which can be reacted with the stabilized Hgb is a starch which has been converted to yield a mono-, di-, tri-, or tetra-aldehyde. In accomplishing this, a hydroxyethyl starch or a dextran, with a molecular weight between 60,000 and 500,000 daltons, is dissolved in water with a concentration of from 2 to 10%. Cyanogen bromide in acetonitrile, in a concentration of 8 to 40%, by volume, is added to the hydroxyethyl starch solution. The ratio of cyanogen bromide to hydroxyethyl starch is from 0.05 to 0.15 gram of cyanogen bromide per gram of hydroxyethyl starch. The combined solution is maintained at a pH of 9 with sodium hydroxide or other soluble hydroxide. After the addition of the cyanogen bromide solution to the hydroxyethyl starch solution is completed, the pH is adjusted to 10.5, employing sodium hydroxide or any soluble hydroxide, and the solution is held, at room temperature, for from 5 to 30 minutes.

Employing a concentrated mineral acid, the pH is then lowered to 2.5 and held at this pH for 1 to 5 minutes, after which sufficient diamine or mineral acid is added, dropwise, to maintain the pH between 8 and 9. Suitable amines are ethylene diamine or tri(2-amino ethyl) amine. Any suitable mineral acid is appropriate. If the pH is lower than 8, a final pH adjustment to 9.5 is then made with sodium hydroxide.

The temperature of the mixture is reduced to from room temperature to 4° C. and is held at that temperature for from 12 to 24 hours. The solution is then dialyzed against water employing dialysis tubing. A solid bicarbonate is added to the resulting solution to obtain a pH of 8.5. Among the bicarbonates which can be employed are sodium bicarbonate, potassium bicarbonate, or ammonium bicarbonate. A small amount of glutaraldehyde or any linear dialdehyde is then added slowly, maintaining a pH of 8.0, for at least 2 hours. This mixture is then dialyzed against water using dialysis tubing, resulting in the monoaldehyde form of hydroxyethyl starch.

The dialdehyde form of hydroxyethyl starch can be formed beginning with the same 2 to 10% aqueous solution of hydroxyethyl starch, and adding a 2.5% aqueous solution of a periodate, with thorough mixing. The amount of periodate added is from 0.25 to 1 gram for each gram of hydroxyethyl starch. Among the periodates which can be employed are sodium periodate, potassium periodate or ammonium periodate. The resulting solution is cooled to from room temperature to 4° C., while protecting it from light, and is held at that temperature for 12 to 48 hours. It is then dialyzed, exhaustively, employing dialysis tubing, against water.

To form the trialdehyde form of hydroxyethyl starch, the monoaldehyde form of the material, as described above, is treated with the periodate in the manner just described.

The acellular resuscitative fluid can be formed from any of the aldehyde polymers just described and either of the stabilized hemoglobin materials described. To accomplish this, the aldehyde polymer is dissolved in distilled, deionized, or demineralized water to a concentration of 0.4 to 1%. The pH of the solution is buffered to 8.0 employing a solid bicarbonate. The solution is then mixed with the stabilized hemoglobin, which is in an aqueous solution at a concentration of from 5 to 12.5%. From 1 to 5 grams of the stabilized hemoglobin are employed for each gram of the aldehyde polymer.

The resulting mixture is retained at room temperature for from 24 to 48 hours.

A borohydride, in concentration of 0.1 to 1 gm per gram of polymer, is then added to the polymer-Hgb solution, with stirring, at room temperature, for from 12 to 24 hours, resulting in the final product. The resulting solutions are then dialyzed against water employing dialysis tubing, and the dialysis unit employed is one which has a molecular weight cut off to pass the unreacted Hgb. The color of the dialyzate indicates the amount of hemoglobin complex present, but not bound to the aldehyde polymer. The dialysis is continued until a colorless solution results.

The aldehyde polymer stabilized hemoglobin can be reduced to a powdered form employing standard freeze-drying techniques, such as temperatures of from $-50°$ to $-65°$ C. and pressures of from 10 to 50 millitorr.

The following examples illustrate the formation of the materials of the present invention. All amounts, unless otherwise designated, are by weight.

EXAMPLE 1

A solution was prepared consisting of 105 parts, by weight, Tetronic 1307 (BSAF Wyandotte Corp., Wyandotte, MI), in dimethyl sulfoxide. The solution was formed at room temperature. To this solution was added 0.6 part dicyclohexyl carbodiimide along with 0.05 part phosphoric acid, and the solution was stirred overnight. The mixture was then dialyzed using dialysis tubing against water for twenty-four hours. During this period, several water changes were made. The dialysis precipitated the unused materials which were separated by filtration. The infra-red spectra indicated the presence of the aldehyde formation and is consistent with the tetra-aldehyde polymer. 20 parts were produced.

EXAMPLE 2

12.5 gm of hydroxyethyl starch (HES) is dissolved in 600 ml. water. To this solution, 1.5 gm. of cyanogen bromide, dissolved in 18 ml. of acetonitrile, was added, maintaining the pH at 9 with 1N NaOH. Upon completion of this addition, the pH was adjusted to 10.5 with NaOH and kept at this value for 5 minutes. Using concentrated HCl, the pH was lowered to 2.5 for one minute. 12 ml. of diaminoethane was added drop-wise to keep the pH between 8 and 9. A final pH adjustment to 9.5 is made with 1N NaOH. This mixture was kept at 4° C. overnight. The solution was then dialyzed with dialysis tubing against water. Solid NaHCO$_3$ was added to the solution to obtain a pH of 8.5. 2 ml. of a 50% glutaraldehyde solution was added drop-wise, maintaining the pH at 8.0, for two hours. This mixture was dialyzed with dialysis tubing against water, yielding 10 gm. of the monoaldehyde form of hydroxyethyl starch.

EXAMPLE 3

6.2 gm of HES was dissolved in 250 ml. of water. To this solution, 6.0 gm. of NaIO$_4$ was added with thorough mixing. This solution was protected from the light and kept at 4° C. for twenty-four hours. The mixture was dialyzed exhaustively with dialysis tubing against distilled water, producing 5 gm. of the dialdehyde form of hydroxyethyl starch.

EXAMPLE 4

The dialyzed solution resulting from Example 2 is treated in the manner outlined in Example 3; the result is the trialdehyde form of hydroxyethyl starch.

EXAMPLE 5

The arginine residues of Hgb were modified with 1,2-cyclohexanedione in a sodium borate buffer. The Hgb solution (5 gm./100 ml.) was adjusted to a pH of 9.0 with a sodium borate buffer. Then 0.1 gm of 1,2-cyclohexanedione was added and the pH maintained at 9.0. The reaction mixture was kept at 37° C. for one hour under an atmosphere of nitrogen. Dialysis against distilled water using dialysis tubing at 4° C. gives 4.5 gm. of the modified Hgb, which is called Hgb-Cyclo.

EXAMPLE 6

Glyoxalic acid (0.1 gm. in 20 ml. H$_2$O) was neutralized to pH 7 with 0.1 N NaOH. Then 0.5 gm. of NaCNBH$_3$ was added to this solution. The pH of a Hgb solution (5 gm./100 ml.) was adjusted to pH 7 with a phosphate buffer. The two solutions were combined and maintained at pH 7 for one-half hour at room temperature. The solution was dialyzed with dialysis tubing against distilled water at 4° C. resulting in 4.5 gm. of modified Hgb termed Hgb-Gly.

EXAMPLES 7-14

Each one of the aldehyde polymers—mono-, di-, tri-, and tetra - (0.4 gm./100 ml.) was dissolved in distilled water. The pH of these solutions was maintained at 8.0 by the addition of solid NaHCO$_3$. Each solution was mixed with Hgb-Gly or Hgb-Cyclo (5 gm./100 ml.) in a ratio of 0.05 to 0.5, at room temperature, overnight. Then 1 gm. NaCNBH$_3$ was added with stirring at room temperature for two hours. The solutions were then dialyzed exhaustively with dialysis tubing against distilled water using a dialysis unit with a molecular weight cut-off of 100,000. The color of the dialyzate indicated the amount of the Hgb-Gly or Hgb-Cyclo present and not bound to the aldehyde polymer. The process was continued until a colorless solution resulted. All of the samples were reduced to powdered form by the process of freeze-drying.

EXAMPLE 15

In order to estimate the basic immunogenic properties of the hemoglobin polymers used in transfusion studies, Agar Gel Immunodiffusion (AGID) testing was performed in the following manner:

Rabbit Sensitization: Ten New Zealand white young adult male rabbits were divided into 2 groups and immunized according to the following schedules:

Group I: On day #1, hind foot pads and intracutaneous sites on the neck and axillae of each animal were injected with the following preparation:
500 ug polymer HES-(L)-Trial-Hgb-Gly - KLH conjugate where KLH is keyhole limpets hemocyanin
0.5 ml. phosphate buffered saline
0.5 ml. Al(OH)$_3$ slurry
which was stirred for 60 minutes at 4° C. and emulsified in 1 ml. Complete Freund's Adjuvant (CFA), yielding a total volume of 2.3 ml. These injections were repeated on day 56. On day 112 the animals were injected intramuscularly with 2 ml. of 500 ug conjugate, 1 ml. phosphate buffered saline, and 1 ml. of incomplete Freund's adjuvant. Fourteen days after this injection, blood was collected via the central ear artery, the sera extracted and frozen in 2 ml. vials. The sera were used as the negative control.

Group II: Each rabbit in this group received an initial injection of 5 mg. of conjugate (keyhole limpets hemocyanin) in 2.5 ml. of phosphate buffered saline with 2.5 ml. of CFA in the hind foot pads and 5 other intramuscular and subcutaneous sites. Twenty-eight days later, each animal received a 1.5 ml. injection of 500 ug of the same conjugate in phosphate buffered saline via the marginal ear vein. These intravenous injections were repeated on day 42. Sera were obtained on day 52 and handled in the same manner as Group I, extracted and frozen. The polymer used in preparation of the conjugate was HES-(L)-Trialdehyde-Hgb-Gly.

Polymers presently in use have been screened against each of these two sera preparations using standard AGID techniques. In no instance have any positive reactions been observed. Normal rabbit serum has been used as a negative control and, since there are no known positives, anti rat IgG (Sigma Chem.) was plotted against rat IgG obtained in house to check the validity of the plate and proper performance of the procedure.

EXAMPLE 16

In order to evaluate the oxygen transport properties of the acellular resuscitative fluids, the technique of biotonometry was used. The results are presented in Table 1.

TABLE 1

Oxygen Saturation Data $$\text{Percentage Saturation} = \frac{KP^n}{1 + KP^n}$$

| | $P_{50}$ | n | K |
|---|---|---|---|
| Hgb | 14.9 | 1.86 | $6.6 \times 10^{-3}$ |
| Hgb—Gly | 37.8 | 1.72 | $1.97 \times 10^{-3}$ |
| HES—monoaldehyde-Hgb—Gly | 32.6 | 1.52 | $4.97 \times 10^{-3}$ |
| HES—Dialdehyde-Hgb—Gly | 12.7 | 1.16 | $5.2 \times 10^{-3}$ |
| HES—Trialdehyde-Hgb—Gly | 35.0 | 1.50 | $4.8 \times 10^{-3}$ |
| Hgb—Cyclo | 27.4 | 1.14 | $2.2 \times 10^{-2}$ |
| HES—Trialdehyde-Hgb—Cyclo | 34.0 | 1.06 | $2.4 \times 10^{-2}$ | where:
K = affinity constant
n = Hill constant
P = saturation presssure (torr)
$P_{50}$ = half saturation pressure

EXAMPLE 17

To confirm the results presented in EXAMPLES 7–14, that is, that a compound was actually formed in the synthetic process, it was necessary to use the technique of electrophoresis. This process is based upon the net electrical charge on the resulting compound. The procedure involved placing a drop of the resuscitative fluid on a cellulose acetate plate which had been treated with a proper buffer. The moist plate was then placed between two electrodes having a potential difference of between 150 and 200 volts. This process was continued for 10 to 20 minutes. Once the process was complete, the cellulose acetate plate was stained with Ponceau Red dye. After developing, the optical densities of these patterns were measured with a scanning densitometer. Using the hemoglobin as a standard reference, the changes occurring in the synthetic process were readily documented visually. Some of these results are shown in FIG. 1, where the optical density, in arbitrary units, is plotted against chart distance in centimeters. This figure illustrates the optical density patterns for Hgb, Hgb-gly and compounds synthesized from the mono-, di-, tri-, and tetra-aldehydes. These patterns are consistent with the synthesis.

EXAMPLE 18

This example was designed to illustrate the in vivo administration of the acellular resuscitative fluid. The significance of this investigation deals with the survival rate. In all cases, the freeze-dried powder was reconstituted with 0.9% NaCl solution containing 80 mg/100% nicotinamide adenine dinucleotide (NADH), and nicotinamide dinucleotide phosphate (NADPH) at 80 mg/100%. Three common laboratory rats were used in this exchange-transfusion. In each case, 1 cc. of blood was removed from the rat and replaced with 1.5 cc. of the synthetic acellular resuscitative fluid. This process was repeated each five minutes until the desired replacement was attained. In the first rat, 50% of the blood was removed; in the second, 75%; and in the third, 95%. After the exchange-transfusion, the rats were placed in individual metabolic cages and given food and water ad libitum. All of the rats survived the exchange-transfusion experiment.

EXAMPLE 19

Figure 2:
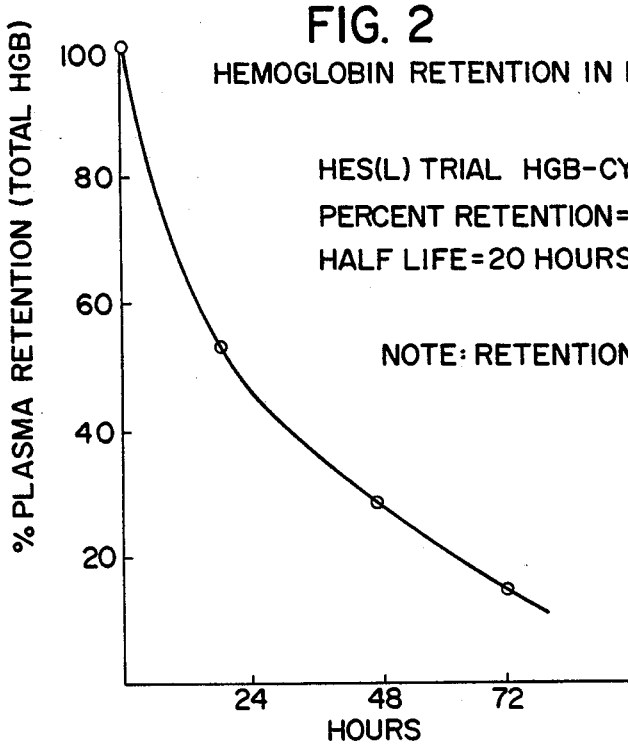
FIG. 2 illustrates percentage plasma retention over a period of hours.
Figure 3:
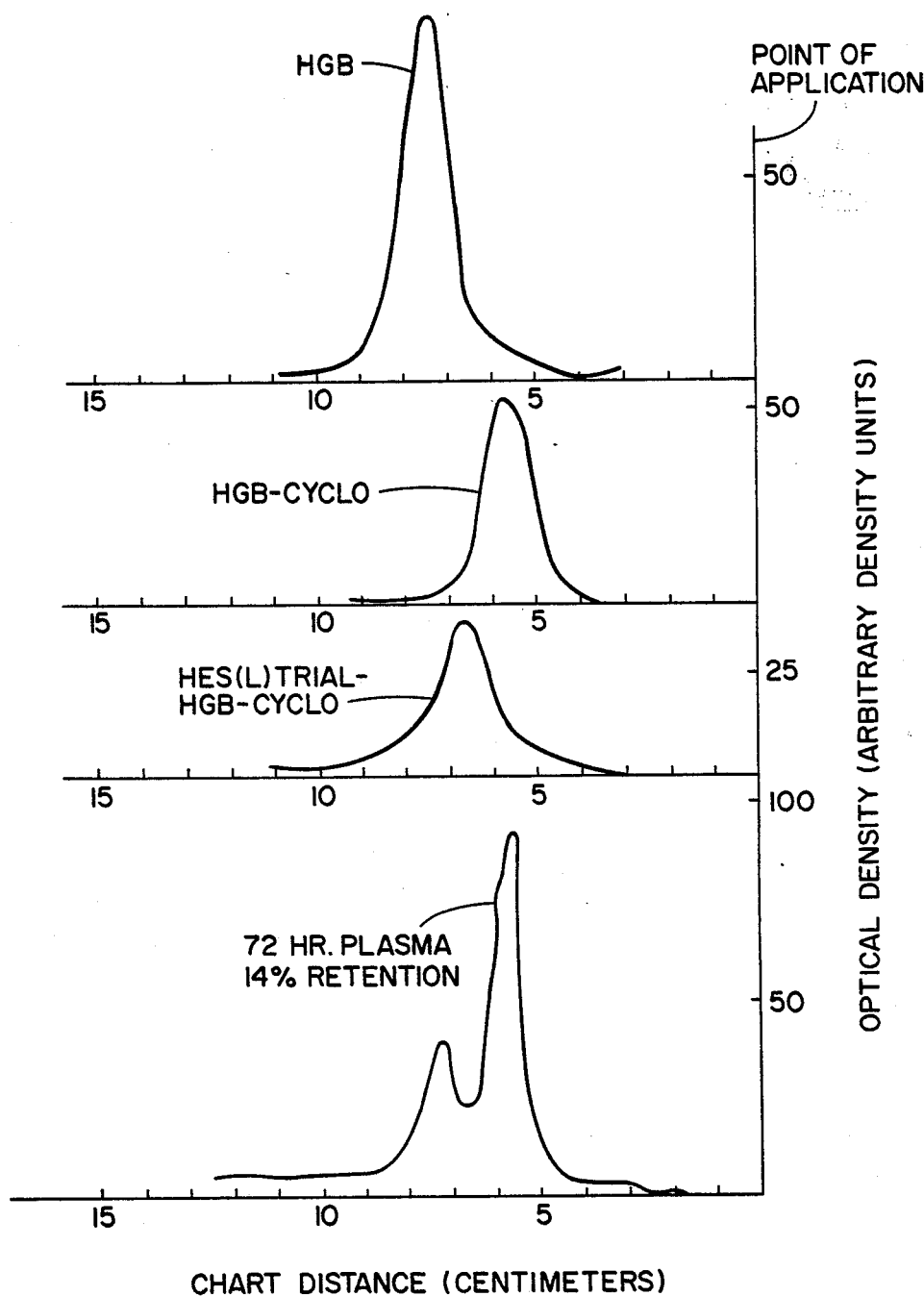
FIG. 3 is an illustration of the optical density of the acellular resuscitative fluid against chart distance.

The procedure of this example essentially repeats the work of Example 18. The purpose was to examine the retention times in the circulation of the synthetic material. The exchange-transfusion was performed in five common laboratory rats at a 50% replacement level. At the completion of the experiment the rats were returned to individual metabolic cages. During the recovery period, blood samples were removed from the rats and the plasma was analyzed. This plasma analysis involved the determination of the total hemoglobin remaining after the transfusion and an electrophoresis pattern of the plasma components. The hemoglobin was evaluated spectrophotometrically by the cyanomethemoglobin method. The method used for the electrophoresis is explained in EXAMPLE 17. FIG. 2 shows the results of the hemoglobin retention times in the plasma for a seventy-two hour time period. The electrophoretic optical density patterns for the starting materials and the reference hemoglobin are presented in FIG. 3, where the optical density, in arbitrary units, is plotted against chart distance in centimeters.

While specific materials have been shown and described, they should not be considered as limiting, in any way, the full scope of the invention as set forth in the appended claims.

I claim:
1. An acellular resuscitative fluid comprising the reaction product of:
   (a) A stroma-free hemoglobin which has been modified to provide reactive groups selected from the class consisting of oxyacids and diketones; and
   (b) a high molecular weight polymer, having reactive aldehyde constituents, selected from the class consisting of:
      (1) hydroxyethyl starch having a molecular weight of from 60,000 to 450,000 daltons; and
      (2) a Tetronic polymer having a molecular weight of from 1,650 to 27,000 daltons which is a block copolymer formed by the addition of ethylene and propylene oxide units to ethylene diamine.

2. The acellular resuscitative fluid of claim 1 wherein the high polymer is in the form of a monoaldehyde.

3. The acellular resuscitative fluid of claim 1 wherein the high polymer is in the form of a dialdehyde.

4. The acellular resuscitative fluid of claim 1 wherein the high polymer is in the form of a trialdehyde.

5. The acellular resuscitative fluid of claim 1 wherein the high polymer is in the form of a tetraaldehyde.

6. The acellular resuscitative fluid of claim 1 wherein the high polymer is a hydroxyethyl starch modified by molecular substitution by hydroxyethylation to a degree of from 0.2 to 0.9.

7. The acellular resuscitative fluid of claim 1 wherein the high polymer is a Tetronic polymer which is a block copolymer of ethylene oxide and propylene oxide units reacted with an ethylene diamine base.

8. A powdered acellular resuscitative material formed by freeze-drying the reaction product of:
   (a) a stroma-free hemoglobin which has been modified to provide reactive groups selected from the class consisting of oxy-acids and diketones; and
   (b) a high molecular weight polymer, having reactive aldehyde constituents, selected from the class consisting of:
      (1) hydroxyethyl starch having a molecular weight of from 60,000 to 450,000 daltons; and
      (2) a Tetronic polymer having a molecular weight of from 1,650 to 27,000 daltons which is a block copolymer formed by the addition of ethylene and propylene oxide units to ethylene diamine.

9. The powdered acellular resuscitative material of claim 8 wherein the high polymer is in the form of a monoaldehyde.

10. The powdered acellular resuscitative material of claim 8 wherein the high polymer is in the form of a dialdehyde.

11. The powdered acellular resuscitative material of claim 8 wherein the high polymer is in the form of a trialdehyde.

12. The powdered acellular resuscitative material of claim 8 wherein the high polymer is in the form of a tetraaldehyde.

13. The powdered acellular resuscitative material of claim 8 wherein the high polymer is a hydroxyethyl starch modified by molecular substitution by hydroxyethylation to a degree of from 0.2 to 0.9.

14. The powdered acellular resuscitative material of claim 8 wherein the high polymer is a Tetronic polymer which is a block copolymer of ethylene oxide and propylene oxide units reacted with an ethylene diamine base.

15. A method for forming a powdered acellular resuscitative material comprising:
   a. reacting
      (1) A stroma-free hemoglobin which has been modified to provide reactive groups selected from the class consisting of oxyacids and diketones; and
      (2) a high molecular weight polymer, having reactive aldehyde constituents, selected from the class consisting of:
         (a) hydroxyethyl starch having a molecular weight of from 60,000 to 450,000 daltons; and
         (b) a Tetronic polymer having a molecular weight of from 1,650 to 27,000 daltons which is a block copolymer formed by the addition of ethylene and propylene oxide units to ethylene diamine; and
   b. freeze-drying the resulting material.

16. The method of claim 15 wherein the high polymer is in the form of a monoaldehyde.

17. The method of claim 15 wherein the high polymer is in the form of a dialdehyde.

18. The method of claim 15 wherein the high polymer is in the form of a trialdehyde.

19. The method of claim 15 wherein the high polymer is in the form of a tetra aldehyde.

20. The method of claim 15 wherein the high polymer is a hydroxyethyl starch modified by molecular substitution by hydroxyethylation to a degree of from 0.2 to 0.9.

* * * * *